(12) United States Patent
Altmeyer et al.

(10) Patent No.: US 10,035,816 B2
(45) Date of Patent: Jul. 31, 2018

(54) COMPOUND FOR TREATING RESPIRATORY SYNCYTIAL VIRUS INFECTION AND PREPARATION METHOD AND USE THEREOF

(71) Applicant: SHANDONG UNIVERSITY, Shandong (CN)

(72) Inventors: Ralf Altmeyer, Shandong (CN); Jingjing Cao, Shandong (CN)

(73) Assignee: SHANDONG UNIVERSITY, Shandong (CN)

( * ) Notice: Subject to any disclaimer, the term of this patent is extended or adjusted under 35 U.S.C. 154(b) by 0 days.

(21) Appl. No.: 15/834,945

(22) Filed: Dec. 7, 2017

(65) Prior Publication Data

US 2018/0094021 A1   Apr. 5, 2018

Related U.S. Application Data

(63) Continuation of application No. PCT/CN2017/073133, filed on Feb. 9, 2017.

(30) Foreign Application Priority Data

Feb. 14, 2016  (CN) .......................... 2016 1 0084979

(51) Int. Cl.
*C07J 69/00* (2006.01)
*A61K 31/58* (2006.01)
*A61P 31/14* (2006.01)

(52) U.S. Cl.
CPC .............. *C07J 69/00* (2013.01); *A61K 31/58* (2013.01); *A61P 31/14* (2018.01)

(58) Field of Classification Search
CPC .................................. C07J 69/00; A61K 31/38
See application file for complete search history.

(56) References Cited

U.S. PATENT DOCUMENTS

| | | | | |
|---|---|---|---|---|
| 6,432,970 B2* | 8/2002 | Beachy | .................. | A61K 31/00 514/278 |
| 7,098,196 B1* | 8/2006 | Beachy | ................ | C07D 491/10 435/4 |
| 7,291,626 B1* | 11/2007 | Beachy | .................. | A61K 31/00 514/278 |
| 7,476,661 B2* | 1/2009 | Beachy | ................ | C07D 491/10 435/4 |

FOREIGN PATENT DOCUMENTS

| | | |
|---|---|---|
| CN | 105232562 A | 1/2016 |
| WO | 2006026430 A2 | 3/2006 |
| WO | 2008083248 A2 | 7/2008 |

OTHER PUBLICATIONS

Bailly, B. et al. "Targeting human respiratory syncytial virus transcription antitermination factor M2-1 to inhibit in vivo viral replication" Scientific Reports, No. 6, May 19, 2016, pp. 1-11.
International Search Report dated May 31, 2017 issued in International Application No. PCT/CN2017/ 073133 and English Translation.
Zhou, Jianxia et al. "Advances in the Research of a Sterodial Alkaloid Cyclopamine" Chines Journal of Natural Medicines, vol. 4, No. 6, Nov. 30, 2006, pp. 468-472 (Abstract only).

* cited by examiner

*Primary Examiner* — Golam M Shameem
(74) *Attorney, Agent, or Firm* — Troutman Sanders LLP

(57) ABSTRACT

The present invention declares a kind of compound to treat respiratory syncytial virus infection and its preparation method and application. The compound stated is cyclopamine's chemical analogs, has the property of inhibiting respiratory syncytial virus replication, and does not have the property of inhibiting Hedgehog signaling pathways. The preparation method stated is to get the cyclopamine's chemical analogs through drug chemical synthesis, then to screen the analogs with two parallel in vitro experiment. The compound described can be used to treat respiratory virus infection, paramyxovirus, respiratory syncytial virus infection, capillary bronchitis/pneumonia/tympanitis caused by respiratory syncytial virus. Furthermore, the compound described never cause the side effects of fetal malformation, and it overcame the teratogenicity of cyclopamine, and filled the gap of anti-human respiratory syncytial virus drug, especially of the field of pediatric drug.

8 Claims, 3 Drawing Sheets

Figure 1:
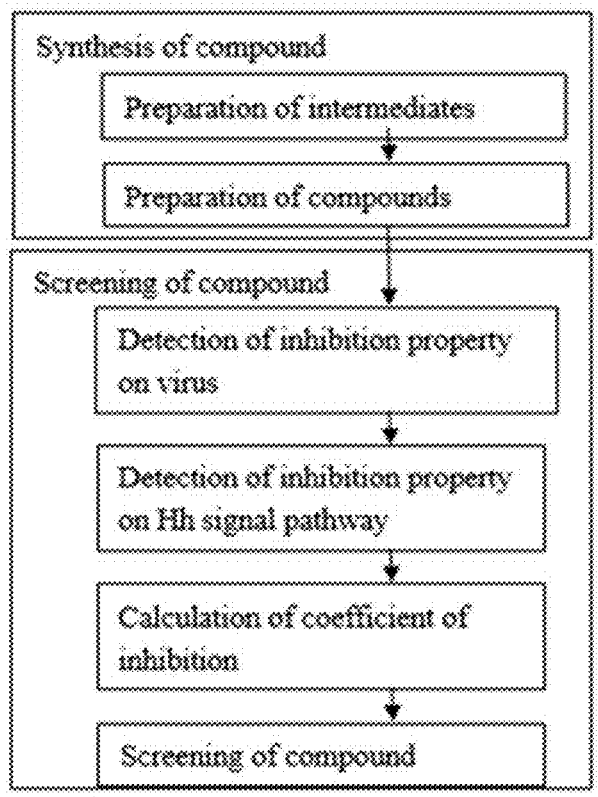

COMPOUND FOR TREATING RESPIRATORY SYNCYTIAL VIRUS INFECTION AND PREPARATION METHOD AND USE THEREOF

CROSS REFERENCE TO RELATED PATENT APPLICATIONS

This is a U.S. continuation of International Patent Application No. PCT/CN2017/073133, filed Feb. 9, 2017, which claims benefit of priority to Chinese Patent Application No. 201610084979.4, filed Feb. 14, 2016. The entire contents of these applications are hereby incorporated by reference.

PATENTED TECHNOLOGY

The invention involved biological medical technology field, specifically concerned with preparation method and usage of compounds for Respiratory syncytial virus treatment.

BACKGROUND

Bronchiolitis is a severe lower-respiratory tract infectious disease primarily caused by members of the Paramyxoviridae family. Human respiratory syncytial virus (hRSV) is the principal cause of morbidity in children less than 2 years of age as well as the elderly, immuno-compromised and transplant patients. To date, there are neither vaccines nor efficacious approved drugs to prevent or treat hRSV infection. The immuno-prophylactic antibody palivizumab is approved for high-risk patients only such as premature babies and infants suffering from underlying diseases. The broad-spectrum small molecule antiviral ribavirin is available to treat infection, but it has considerable side-effects and limited efficacy. During the past decade, a number of drug candidates targeting hRSV entry or replication steps have been advanced to pre-clinical or clinical development.

The hRSV genomic RNA (vRNA) is packaged by the viral nucleoprotein (N) at all times, forming a N:RNA complex, called nucleocapsid. This ribonucleoprotein complex is used as a template for mRNA transcription and genomic or antigenomic RNA replication by the RNA-dependent RNA polymerase (RdRp), which is composed of 2 major viral proteins: the phosphoprotein P and the large polymerase L. In this complex, the phosphoprotein is an essential co-factor of the L polymerase by binding to L and N and targeting the polymerase L to vRNA. Two co-factors, M2-1 and M2-2, are required for the RdRp to process RNA efficiently during the viral cycle. M2-1 is a tetrameric transcription processivity factor that binds in a competitive manner to RNA and P via its core domain. M2-1 functions as an anti-terminator of transcription that prevents premature termination of transcription both intra- and inter-genetically. Although in vitro experiments have shown that M2-1 binds preferentially to positive-sense viral gene end (GE) and poly-A sequences, the exact mechanisms by which M2-1 improves transcription efficiency is not fully understood.

Recently, cyclopamine (CPM) and jervine were identified as highly potent and selective inhibitors of hRSV replication in vitro. CPM is a well-known antagonist of the smoothened protein (Smo) receptor, a 7-transmembrane receptor of the Sonic hedgehog signaling pathway (Shhp). The Shhp is involved in embryonic development, cell differentiation and tumorigenesis. Cyclopamine is a naturally occurring chemical that belongs to the group of steroidal jerveratrum alkaloids. It is a teratogen isolated from the corn lily (Veratrum californicum) that causes usually fatal birth defects. It can prevent the fetal brain from dividing into two lobes (holoprosencephaly) and cause the development of a single eye (cyclopia). It was caused by inhibiting the hedgehog signaling pathway (Hh).

The teratogenic properties of cyclopamine largely preclude its development as a pediatric drug for the treatment of RSV infections. These properties could lead to serious adverse events in treated patients.

Invention

In order to overcome the teratogenic property of CPM, and to pad the internal space of clinical RSV infection treatment, specially pediatric treatment, the present invention provides a kind of compound for RSV infection treatment and its preparation method and application. The compound described can inhibit RSV replication, and cannot inhibit Hedgehog signaling pathway. Therefore, the compound will be a sage and effective anti-RSV drug for clinic, relieving of teratogenicity.

To access to the goals above, the following technical scheme was designed for the present invention:

A kind of compound to treat RSV infection, which is CPM's chemical analogue, with inhibition property on RSV replication, without inhibition property on Hedgehog pathway.

The compound described is a kind of novel chemical entity, including S1-2, S1-4, and all of the possible cyclopamine chemical analogues, with inhibition of respiratory syncytial virus replication effect and without inhibition of the Hedgehog signaling pathway effect. S1-2 and S1-4 is the two instances therein.

The serial of chemical analogues of CPM structure was published in the Chinese patent CN101631463A. And the same analogues were recorded in American patent US20080293754A1.

A typical CPM structure was showed in formula 1.

A kind of optimized CPM analogue was showed in formula I,

In the formula, $R_1$ is H, OH, alkyl group, sulfonamide group, sulfonyl amino, —OC(O)$R_5$, —N($R_5$)C(O)$R_5$ or glycosyl group;

$R_2$ is H, alkyl group, alkenyl group, alkynyl group, naphthenic base, nitrile group, or heterocyclic alkyl; Or, $R_1$ binds with $R_2$, to form =O, =S, =N(R), =N(N$R_2$) or =C(R)$_2$;

$R_3$ is H, alkyl group, alkenyl group or alkynyl group;

$R_4$ is H, alkyl group, alkenyl group, alkynyl group, naphthenic base, heterocyclic alkyl, aralkyl, ceteroary, alkyl aromatic, halogenated alkyl, —O$R_5$, —C(O)$R_5$, —CO$_2R_5$, —SO$_2R_5$—C(O)N($R_5$)($R_5$), —[C(R)$_{2q}$—$R_5$, —[(W)—N(R)C(O)]q$R_5$, —[(W)—C(O)]$_q$$R_5$, —[(W)—C(O)O]$_q$$R_5$, —[(W)—OC(O)]$_q$$R_5$, —[(W)—SO$_2$]$_q$$R_5$, —[(W)—N($R_5$)SO$_2$]$_q$$R_5$, —[(W)—C(O)N($R_5$)]$_q$$R_5$—[(W)—O]$_q$$R_5$, —[(W)—N(R)]$_q$$R_5$, —W—N$R_5^{3+}$X— or —[(W)—S]$_q$$R_5$;

In which, W is divalent alkyl independently;

R is H or alkyl separately;

q is 1, 2, 3, 4, 5, or 6 independently;

X— is a halogen;

$R_5$ is H, alkyl group, alkenyl group, alkynyl group, aryl group, naphthenic base, heterocyclic alkyl, aralkyl, ceteroary, alkyl aromatic, or —[C(R)$_2$]$_p$—$R_6$; P is 0~6; Or any two $R_5$ on the same substituent group can form a 4~8 member ring containing 0~3 miscellaneous atoms, and the heteroatoms are selected from N, O, S or P; The $R_6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR) or —P(O)(OR)(OR). The limiting condition is that $R_1$ is not hydroxyl or glycosyl group when $R_2$, $R_3$ and $R_4$ is H. Another limiting condition is that $R_1$ and $R_2$ are not C=O when $R_4$ is hydroxyl.

For one selected optimized CPM analogue compound, as shown in formula II,

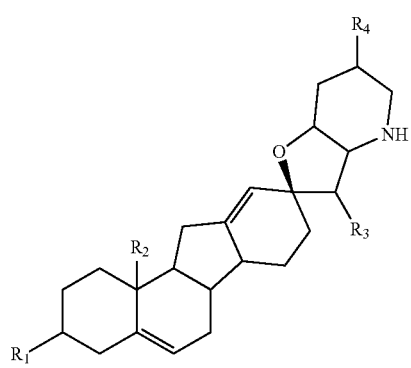

(II)

$R_1$ is H, OH, alkyl group, amidogen, sulfonamide, sulfonamido-, —OC(O)$R_5$, —N($R_5$)C(O)$R_5$ or glycosyl group;

$R_2$ is H, alkyl group, alkenyl group, alkynyl group, aryl group, naphthenic base, nitrile group, heterocyclic alkyl;

$R_3$ is H, alkyl group, alkenyl group, alkynyl group;

$R_4$ is H, alkyl group, alkenyl group, alkynyl group, naphthenic base, heterocyclic alkyl, aralkyl, ceteroary, alkyl aromatic, halogenated alkyl, —O$R_5$, —C(O)$R_5$, —CO$_2R_5$, —SO$_2R_5$—C(O)N($R_5$)($R_5$), —[C(R)$_{2q}$—$R_5$, —[(W)—N(R)C(O)]q$R_5$, —[(W)—C(O)]$_q$$R_5$, —[(W)—C(O)O]$_q$$R_5$, —[(W)—OC(O)]$_q$$R_5$, —[(W)—SO$_2$]$_q$$R_5$, —[(W)—N($R_5$)SO$_2$]$_q$$R_5$, —[(W)—C(O)N($R_5$)]$_q$$R_5$—[(W)—O]$_q$$R_5$, —[(W)—N(R)]$_q$$R_5$, —W—N$R_5^{3+}$X— or —[(W)—S]$_q$$R_5$;

In which, W is divalent alkyl independently;

R is H or alkyl separately;

q is 1, 2, 3, 4, 5, or 6 independently;

X— is a halogen;

$R_5$ is H, alkyl group, alkenyl group, alkynyl group, naphthenic base, heterocyclic alkyl, aralkyl, ceteroary, alkyl aromatic, or —[C(R)$_2$]p-R6; P is 0~6; Or any two $R_5$ on the same substituent group can form a 4~8 member ring containing 0~3 miscellaneous atoms, and the heteroatoms are selected from N, O, S or P; The $R_6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR) or —P(O)(OR)(OR);

In another optimized CPM analogue compound, as shown in formula II, $R_1$ is OH, H, $C_1$~$C_3$ alkyl group replaced or not;

$R_2$ is $C_1$~$C_3$ alkyl group, alkenyl group, alkynyl group replaced or not;

R3 is $C_1$~$C_3$ alkyl group, alkenyl group, alkynyl group replaced or not;

R4 is $C_1$~$C_3$ alkyl group, alkenyl group, alkynyl group replaced or not;

The "replaced" described means that, one or more H in alkenyl group were replaced with substituent as following, $C_1$~$C_{10}$ alkyl group, $C_1$~$C_{10}$ alkoxy, hydroxyl, carboxyl, $C_1$~$C_{10}$ carbonyl, $C_1$~$C_{10}$ acylamino, $C_2$~$C_{10}$ ester group, $C_6$~$C_{30}$ aryl group, halogen atom, cyanogroup, thioether group;

Another selected optimized compound, $R_1$ is OH, $R_2$ is methyl, $R_3$ is methyl, $R_4$ is methyl.

The compound S1-2 described in formula III, was modified based on formula II, in which $R_1$ and $R_4$ was replaced.

The compound S1-4 was described in formula IV, which was modified based on formula II, $R_1$ and $R_4$ in formula II was replaced.

And the difference between S1-2 and S1-4 is that $R_1$ in formula II was replaced with different substituent group.

Series 1-2

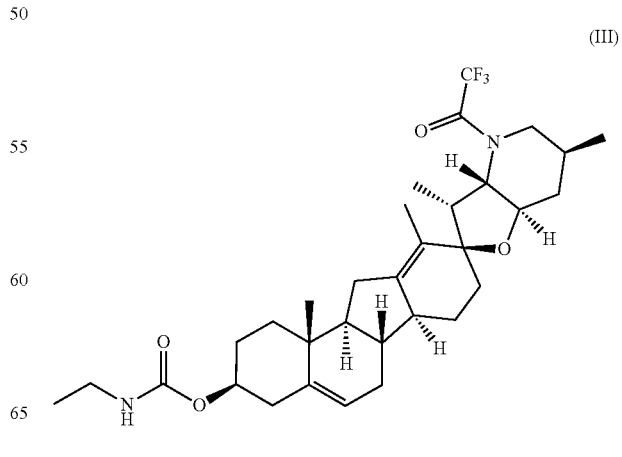

(III)

-continued

Series 1-4

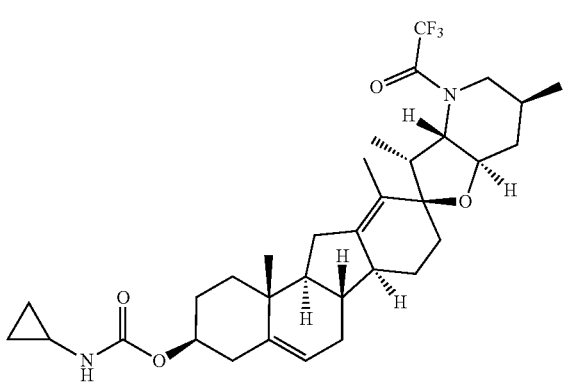

(IV)

A kind of compound preparation method, which was used to treat respiratory syncytial virus infection. The characters of the method are: the chemical synthesis method described to get cyclopamine analogs, and screening analogue by two parallel test in vitro. The described experiments in vitro conducted by two parallel include (1) based on cell experiment, measurement of respiratory syncytial virus replication ability in excitable cells, and (2) based on cell experiment, measurement of a molecular inhibition of sonic hedgehog pathway level, and the inhibition effect is interference level on SAG-induced and Smo-dependent gene transcription.

A method of preparation of compounds for respiratory syncytial virus infection treatment, is characterized by the following steps:
1) Synthetic compounds
2) Screening compounds The preparation method compounds described, consist of two sub-steps:
1) Preparation of intermediates;
2) Preparation compounds The procedure of the compound screening includes four sub-steps:
1) The inhibitory effect of test compounds on the respiratory syncytial virus replication
2) The inhibitory effect of the test compounds on the Hh signal pathway
3) Evaluation respiratory syncytial virus replication and Hh activity inhibition coefficient
4) Screening compounds The preparation procedure of intermediate is as following. First of all, cyclopamine and triethylamine was dissolved in dry dichloromethane DCM; Secondly, under the condition of 0° C., join trifluoroacetic acid anhydride dissolved in DCM into the solution; Thirdly, the reaction mixture slowly heated to a temperature of 15° C. and stirring 16 h. Fourthly, the initial raw materials were confirmed by liquid chromatography-mass spectrometry. Fifthly, concentrate the reaction mixture and dilute the residue with methanol; Sixthly, get the received suspension to be heated to 70° C. and 1 h heat preservation; Seventhly, the reaction mixture cooling to 15° C.; Finally, the intermediate object is white solid by filtration.

The procedure of compounds preparation is as following. First of all, intermediate and triethylamine was dissolved in dry dichloromethane DCM, cooled in ice; Secondly, join trifluoroacetic acid dissolved in DCM into the solution; Thirdly, the reaction mixture slowly heated to a temperature of 45° C. and stirring 48 h. Fourthly, the initial raw materials were confirmed by TLC. Fifthly, concentrate the reaction mixture in vacuum; Sixthly, clean the residue with methanol; Finally, get the compound object with white solid by filtration.

The detection procedure of compound effect on RSV replication inhibiting is as following. Human respiratory syncytial virus Long strain and HEp-2 cells were used for infection assays. Cells were maintained in DMEM, supplemented with penicillin/streptomycin and 10% FBS, and incubated at 37° C., 5% $CO_2$. Virus was passaged in HEp-2 cells in the same conditions, but with 2% FBS. Virus stocks were prepared by infecting confluent HEp-2 cells at a low multiplicity of infection (MOI) of 0.1 for two to three days. Cells and virus-containing supernatant were then subjected to a single freeze/thaw cycle at −80° C. to release cell-bound virus, and the sample was clarified by centrifugation at 2000×g for 10 min at 4° C. The supernatant was homogenized, aliquoted and stored at −20° C.

The anti-hRSV potency of compounds was evaluated by focus reduction assay following the focus forming assay method, which means that titer calculation was based on the wells with 50 to 100 focus forming. Compounds were tested either during virus adsorption for 1 h at 4° C. to investigate viral entry, post-adsorption for 72 h at 37° C. to investigate viral propagation and replication, or during all stages of infection. The concentration of compound resulting in 50% inhibition ($IC_{50}$) of virus replication was determined by focus counting (viral entry) or focus size measurement (viral propagation) and was determined using non-linear regression analysis using GraphPad Prism. To assess the cytotoxicity of compounds, a CellTiter-Glo Luminescent Cell Viability Assay was carried following the manufacturer's instruction in the conditions of the focus reduction assay.

The detection procedure of compound effect on Hh signal pathway inhibiting is as following. NIH3T3 cells are seeded cells in 6 well plates, or 12 well plate one day in advance, with 5% FBS DMEM, without antibiotics per well so that they will be 90~95% confluent at the time of transfection. Plasmids are diluted with Lipofectamine 2000 (total volume is 100-1000 il) and added to each well containing cells and medium, followed by incubation at 37° C. in a $CO_2$ incubator for 48 h. After 48 h transfection, SAG is added to reach a final concentration of 0.5 iM and CPM analogs at various concentrations. At the end of the incubation, cells are washed, lysed and lysate transferred to a 96-well white plate. LAR II reagent is added (from Promega, Dual-luciferase reporter assay system) and samples read in a luminescence reader. Selected compounds from the antiviral RSV assay were tested in the Hh assay in which the ability of the analog to trigger a CPM-like response (inhibition of Smo-dependent SAG induced gene expression).

In the Hh signal pathway inhibition detection assay, the CPM analogs tested is selected from anti-RSV assay and show effective inhibition on RSV replication. With Hh signal pathway inhibition assay, the effect of the CPM analogs on SAG-induced and Smo-dependent gene expression was analyzed, which is similar to CPM, but with various level.

To assess the differential Hh pathway inhibition vs. replication inhibition of analogs (cpd), we determined a coefficient of inhibition (ICrh).

$$ICrh = \frac{Cdp\ (\%\ RSV\ inhibition/\%\ Hh\ inhibition)}{CPM\ (\%\ RSV\ inhibition/\%\ Hh\ inhibition)}$$

In the formula we described, the denominator is the ratio of CPM inhibition effect, which means the ratio of inhibition on RSV to inhibition to Hh. The numerator is the ratio of prepared CPM analog inhibition effect. According to the definition of a coefficient of inhibition (ICrh), if the compound tested is CPM, the coefficient is 1. If the compound tested is an analog with a score lower than 1, indicating that is an unfavorable inhibition profile, eg anti-RSV activity is lower, while Hh inhibition is still strong. A score higher than 1 indicates a favorable profile.

The substep of screening compounds is that selecting the compounds with ICrh data larger than 1, and filtering out the compounds with ICrh data smaller than 1. Furthermore, the compounds with larger ICrh data will be selected preferentially.

The application of compounds is for treatment of respiratory virus infection disease. Briefly, the diseases consist respiratory virus infection, paramyxovirus, respiratory syncytial virus infection, capillary bronchitis/pneumonia/tympanitis caused by respiratory syncytial virus. Furthermore, the compounds never cause side effects on patients, such as fetal anomaly.

The advantage and beneficial effect of the invention is as following:

1) The compounds provided in this invention can be used in the diseases following treatment effectively, including respiratory virus infection, paramyxovirus, respiratory syncytial virus (RSV) infection, capillary bronchitis/pneumonia/tympanitis caused by respiratory syncytial virus.

2) the compounds provided in this invention never cause side effects on patients, such as fetal anomaly.

3) the preparation method provided in this invention can be used to synthesize various kind of compounds for RSV infection treatment, without side effects absolutely.

4) The preparation methods provided in the invention is easy to do, and with wide material source, low production cost, high economic value.

5) The compounds provided in the invention padded the inter space of RSV infection treatment drug, especially for the pediatric drug. Therefor, it is full of important social value.

DESCRIPTION OF FIGURES

A further explanation of the invention is illustrated by the attached figures and example.

FIG. 1 shows the preparation method flow diagram described in the invention.

FIG. 2 shows the flow diagram of intermediate preparation described in the invention.

FIG. 3 shows the flow diagram of compound preparation described in the invention.

FIG. 4 shows the effect of compounds described in the invention on RSV replication.

As shown in the figure, compounds were tested at 2 concentrations (2 ìM, 8 ìM) in the RSV replication assay. The control (compound-free) is scored at 100% replication. Replication in the presence of CPM is scored at 0% replication. Replication inhibition by analogs S2-6 and C2-2 to C2-4 are scored % inhibition of control.

FIG. 5 shows the effect of compounds described in the invention on Smo associated induced gene expression.

Figure shows that compounds were tested at 10 uM in the hedgehog (Hh) assay. The control (compound-free, presence of SAG) is scored at 100% gene expression. The gene expression in the presence of CPM is significantly reduced by 56%. Gene expression inhibition by analogs S1-2 and S1-4 however are not significant, with 36% and 5% respectively. These data show the proof of principle that the anti-RSV activity of steroidal alkaloid molecules derived from CPM can be dissociated from the inhibitory activity of the Smo-dependent Hh pathway.

FIG. 6 shows the Inhibition of coefficient (ICrh) of CPM and its analogs.

EXAMPLE 1

The preparation of CPM analog S1-2, referring to FIGS. 1, 2, and 3, and the procedure is as following:

1) Cyclopamine (498.06 mg, 1.21 mmol, 1.00 eq) and Et3N (489.76 mg, 4.84 mmol, 4.00 eq) were dissolved in dry DCM (4 ml). Then TFAA (762.41 mg, 3.63 mmol, 3.00 eq) in DCM (1 ml) was added at 0° C. The reaction mixture was warmed slowly to 15° C. and stirred for another 16 h. LCMS showed started material was almost consumed completely. (Desired product RT=0.996 min, 25%; di-CF3CO byproduct RT=1.125 min, 47%). The reaction mixture was concentrated and the residue was diluted with MeOH (15 ml). The resulted suspension was heated to 70° C. for 1 h. Then the reaction mixture was cooled to 15° C. The undissolved solid was collected by filtration. Intermediate (346.00 mg, 681.60 ìmol, 56.33% yield) was obtained as white solid, used for next step without further purification.

2) Preparation of Compound S1-2. Firstly, 130.00 mg, 256.09 umol, 1.00 eq) and TEA (182.00 mg, 1.80 mmol, 7.02 eq) were dissolved in DCM (2 ml), cooled by ice-bath. Then isocyanatoethane (isocyanato ethane) (125.00 mg, 1.76 mmol, 6.87 eq) in DCM (0.5 ml) was added. Then the reaction mixture was stirred at 45° C. for 48 h. TLC showed started material was consumed completely. The reaction was concentrated under vacuum. The residue was washed with MeOH (2.5 ml). Desired product was collected by filtration. Series 1-2 (30.00 mg, 51.84 ìmol, 20.24% yield) was obtained as white solid. The filtrate was concentrated. The crude product was used for next step.

3) Detection of effect of compound on RSV replication. Human respiratory syncytial virus Long strain (ATCC reference VR-26) and HEp-2 cells (ATCC reference CCL-23) were used for infection assays. Cells were maintained in DMEM, supplemented with penicillin/streptomycin and 10% FBS, and incubated at 37° C., 5% $CO_2$. Virus was passaged in HEp-2 cells in the same conditions, but with 2% FBS. Virus stocks were prepared by infecting confluent HEp-2 cells at a low multiplicity of infection (MOI) of 0.1 for two to three days. Cells and virus-containing supernatant were then subjected to a single freeze/thaw cycle at −80° C. to release cell-bound virus, and the sample was clarified by centrifugation at 2000×g for 10 min at 4° C. The supernatant was homogenized, aliquoted and stored at −20° C. The anti-hRSV potency of compounds was evaluated by focus reduction assay following the focus forming assay method, using 50 to 100 focus forming units per well. Compounds were tested either during virus adsorption for 1 h at 4° C. to investigate viral entry, post-adsorption for 72 h at 37° C. to investigate viral propagation and replication, or during all stages of infection. The concentration of compound resulting in 50% inhibition ($IC_{50}$) of virus replication was determined by focus counting (viral entry) or focus size measurement (viral propagation) and was determined using non-linear regression analysis using GraphPad Prism (GraphPad Software, La Jolla Calif. USA). To assess the cytotoxicity of compounds, a CellTiter-Glo Luminescent Cell Viability Assay (Promega, Madison, Wis.) was carried following the manufacturer's instruction in the conditions of the focus reduction assay.

The detailed protocol is as following:

Day1: Seed $2\times10^5$ cells/well in 24-well plate with 0.5 ml 10% FBS DMEM. Incubate at 37° C., 5% $CO_2$ for 16~24 h.

Day2: Compound treatment and virus infection.
1. dilution: the diluent is 25% DMSO, 2% FBS, DMEM. The Compound is diluted to 800 ìM and 200 ìM;
2. Virus dilution: the diluent is DMEM with 2% fetal bovine serum (FBS), hRSV virus stock is P9 ($2.9\times10^7$ pfu/ml) (stored at –80° C.), both thaw it and use it on ice, MOI=0.1.
3. compound treatment and virus infection: Pour off the medium in the 24-well plate (Or rinse once with PBS), add the diluented virus 0.5 ml, and 5 ìl diluented drug to make the virus infection moi=0.1, and the drug concentration is 8 ìM, 2ìM;
4. The plates were incubated at 37° C., 5% $CO_2$ for 3 days (observe the CPE)

Day4: Seed new Hep2 cells for titration Seed HEp-2 cells in new 24-well plates with $1.5\times10^5$ cells/well. Incubate at 37° C., 5% $CO_2$ for 16~24 h Day5: Collect virus and virus titration
1. Put the 24-wells plates in –80° C. freezer for 1 h, and then thaw them on ice, collect the virus in wells into tubes (on ice). Centrifugate these tubes with 8000 rpm, 5 min, and then pipette out 50 μl into a new tubes to test virus titer and then the rest virus samples were pipetted into 2 ml prechilled tube (on ice) then fast frozen in liquid nitrogen and storaged in –80° C. freezer.
2. Virus dilution: Prepare six 1.5 ml EP tube, mark, on ice. Add 270 μl 2% medium in each tube. From stock, 30 μl virus in 270 μl 2% medium serial dilution to get $10^{-1}$ to $10^{-6}$ virus dilutions
3. Remove cell culture medium, and rinse once with PBS (on ice);
4. Infect monolayer HEp-2 cells with 200 μl virus dilutions correspondingly.
5. Incubate for about 1.5 h in the incubator at 37° C., 5% $CO_2$. Shake every 15 min
6. Water bath the overlay medium (DMEM with 2% FBS and 0.8% CMC) at 37° C. for 1 h, then pipette out virus solution after the 1.5 h of virus incubation time, and wash twice with PBS. Add DMEM with 2% FBS and 0.8% CMC per well. Incubate for 3-4 days at 37° C., 5% $CO_2$.

Figure 4:
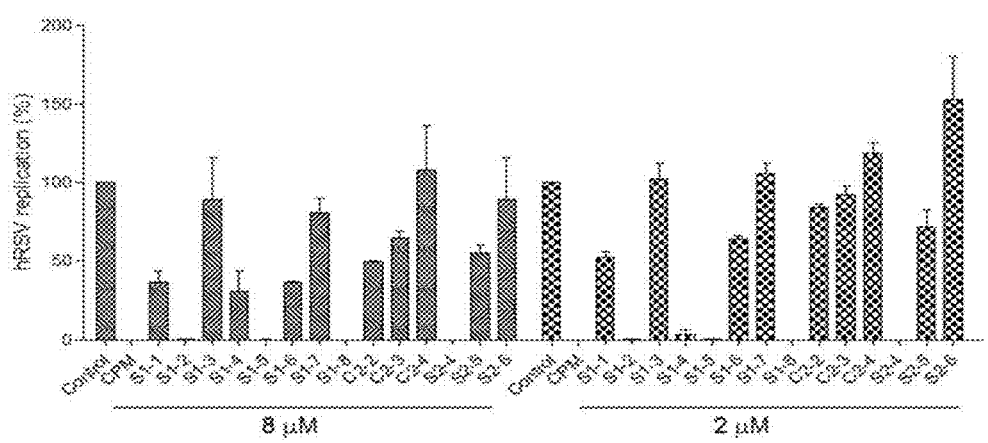

Day8:
1. Pipette out CMC and wash once with PBS (on ice);
2. Fix the cells with 4% PFA for at least 20 min, then wash with PBS, and air dry;
3. Incubate the cells with 0.25% tritonX-100 in PBS for 20 minutes. Wash the plate with PBS for 3 times, and every wash lasts for 4 min;
4. Incubate the cells for about 1 hour at RT with 200 μl of primary anti-hRSV F antibody (mouse-Fizgerald, Acton, Mass.) diluted 1:1000 in PBS-5% skim milk;
5. Wash 3×4 min with PBS-0.02% Tween 20;
6. Apply a 1:6000 dilution (200 μl) of secondary HRP-conjugated antibody (goat anti-mouse-Bethyl, Montgomery, Tex.) in PBS-5% skim milk and incubate at room temperature for 1 h.
7. Wash the monolayers with PBS-0.02% Tween 20 for 3 times, and every wash lasts for 4 min
8. Apply 200 μl of True Blue substrate and leave at room temperature in the dark until blue spots appear (≈more than 10 min);
9. Rinse with running water (PBS will fade the colour);
10. Dry in oven, scan plate and count plaques;

From FIG. 4, compound S1-2 has the maximum inhibition effect on RSV replication is 99% (compared with blank control.)

4) Detection of inhibition effect of compounds on Hh pathway. NIH3T3 cells are seeded cells in 6 well plates ($3\times10^5$ cell/well), or 12 well plate ($1.5\times10^5$ cell/well) one day in advance, with 5% FBS DMEM, without antibiotics per well so that they will be 90~95% confluent at the time of transfection. Plasmids are diluted with Lipofectamine 2000 (total volume is 100~1000 ìl) and added to each well containing cells and medium, followed by incubation at 37° C. in a $CO_2$ incubator for 48 h. After 48 h transfection, SAG is added to reach a final concentration of 0.5 ìM and CPM analogs at various concentrations. After 48 h of incubation with compounds, cells are washed, lysed and lysate transferred to a 96-well white plate. LAR II reagent is added (Promega, Dual-luciferase reporter assay system, E1910) and samples read in a luminescence reader.

The detailed protocol is as following:

Day1: Seed NIH3T3 cells in 6 well plate ($3\times10^5$ cell/well), or 12 well plate ($1.5\times10^5$ cell/well) one day advance, with 5% FBS DMEM, without antibiotics per well so that they will be 90~95% confluent at the time of transfection.

Day2: For each transfection sample, prepare DNA-Lipofectamine 2000 complexes as follows: (the reagent volume and DNA quantity, see the following table);
1. Dilute DNA in 250 ìl of Opti-MEM reduced serum medium with serum. And the DMA is Gli-binding site-luciferase expressing plasmid and *Renilla* luciferase expressing plasmid, with ratio of 50:1. Mix gently.
2. Mix Lipofectamine 2000 gently before use, then dilute the appropriate amount in 250 ìl of Opti-MEM. Mix gently.
3. After the 5 min incubation (not longer than 30 min), combine the diluted DNA with the diluted Lipofectamine 2000 (total volume is 100-1000 ìl). Mix gently and incubate for 20 min at room temperature to allow the DNA-Lipofectamine 2000 complexes to form.
4. Add the DNA-Lipofectamine 2000 complexes to each well containing cells and medium. Mix gently by rocking the plate back and forth.
5. After 4~6 h, pipette out the medium from the well, and growth medium should be replaced. Then incubate the cells at 37° C. in a 5% $CO_2$ incubator for 48 h.

Day4: After 48 h transfection, prepare drug diluent, which is DMEM, with 0.5% FBS, 0.25% DMSO. Then drug preserving fluid was prepared. SAG will be diluted to 1 ìM. And Cyclopamine (CPM) and its analogs will be diluted to 20 ìM. The same well will be added with 250 ìl 1 ìM SAG and 250 ìl 20 ìM CPM or its analogs. The final concentration of SAG is 0.5ìM, and the final concentration of CPM or its analogs is 10 ìM, Day5:
1. Remove growth media from cultured cells. Rinse cultured cells in 1×PBS. Remove all rinse solution.
2. According to the operating manual of the Dual-luciferase reporter kit (Promega, E1910), dispense the recommended volume 100 ìl of 1×PLB into each culture vessels. Gently rock/shake the culture vessel for 15 min at room temperature. Transfer lysate to a 96-well white plate.
3. Add cell lysate 20 ìl to a well and then add 50 ìl LAR II in kit. Read the plate and measure the firefly luciferase activity level.

4. Add 50 ìl stop&Glo reagent, mix them, no bubbles. Read the plate and measure the *Renilla* luciferase activity level.

Record all the data and calculate the ratio. All the luminiscence data will be deducted with blank data. The firefly luciferase activity data in the group with SAG and with DMSO control will be seen as 1, and the data in other group will be normalized. The ratio above will be named as "ratio 1". Then, the *Renilla* luciferase activity data in the group with SAG and with DMSO control will be seen as 1, and the data in other group will be normalized. The ratio above will be named as "ratio 2". Finally a new ratio can be calculated, which is the ratio of "ratio 1" to "ratio 2", and it means that normalized expression level (percentage) of *Renilla* luciferase.

Figure 5:
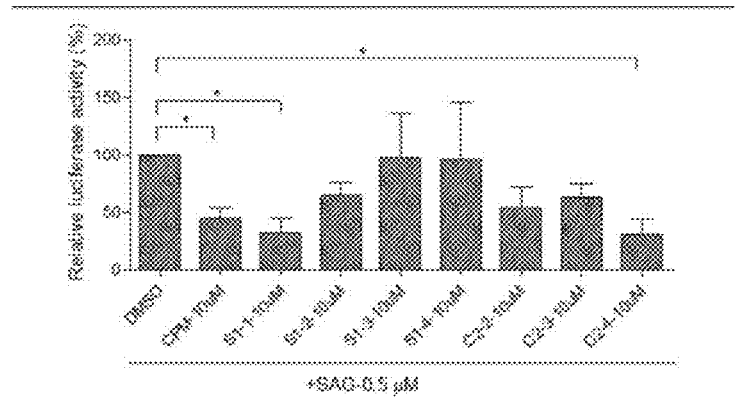

CPM analog S1-2 shows unsignificant inhibition effect on gene expression, with inhibition percentage 36%. The data above indicated that anti-RSV effect can be disassociated with anti-Hh signal pathway the Steroid alkaloids derived from CPM, see the FIG. 5.

Figure 6:
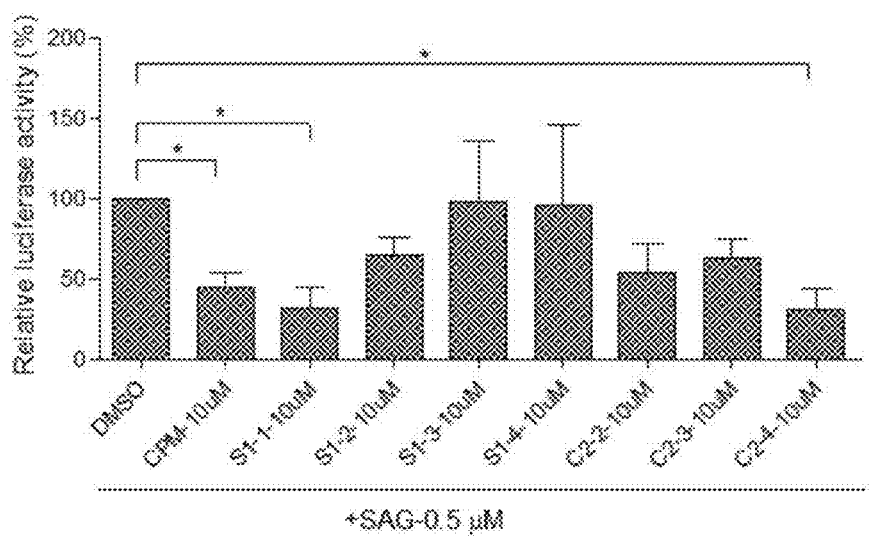

5) Calculate the coefficient of inhibition on RSV replication and Hh activity (ICrh). The ICrh of S1-2 is 1.44596, which is larger than 1 and means that it owns beneficial inhibition property, see the FIG. 6.
6) Screening compound S1-2. compound S1-2, with beneficial inhibition property, can be developed to treat RSV infection see the FIG. 6. Example 2

Figure 2:
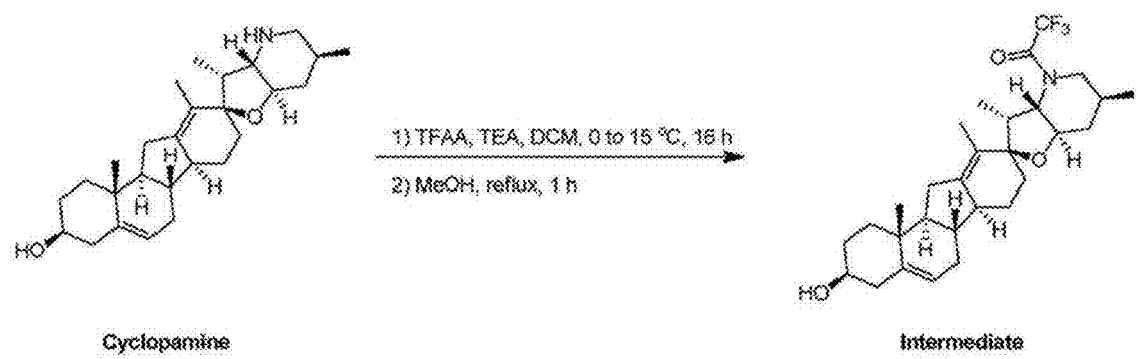
Figure 3:
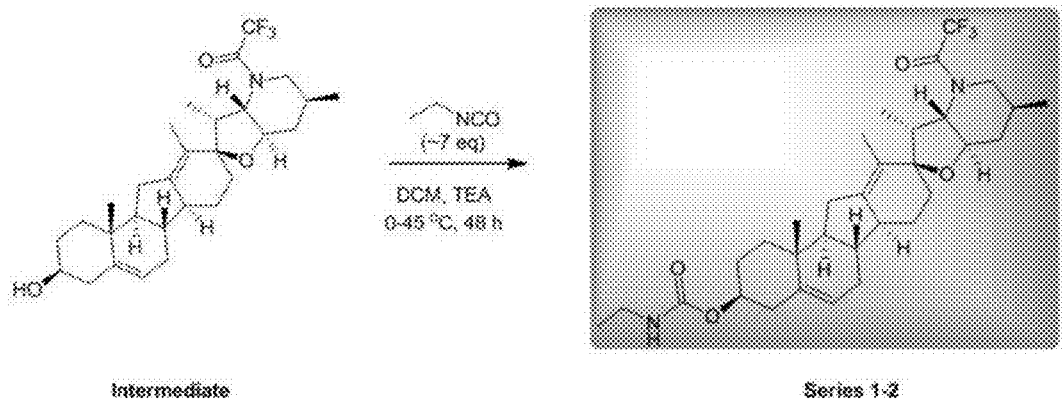

The preparation of CPM analog S1-4, and the procedure is as following: see the FIGS. 1, 2, and 3.
1) Preparation of intermediate. The procedure is as example 1.
2) Preparation of compound S1-4. The procedure is as example 1.
3) Detection of inhibition effect on RSV replication of S1-4. The detection protocol is as example 1. see the diagram 4. The maximum inhibition percentage of S1-4 on RSV replication is 88%, see the FIG. 4.
4) Detection of inhibition effect on Hh signal pathway of S1-4. The detection protocol is as example 1. see the diagram 5. The inhibition effect of CPM analog S1-4 on gene expression is not significant, with inhibition percentage 5%. The data above indicated that, the anti-RSV effect can be disassociated with anti-Hh signal pathway the Steroid alkaloids derived from CPM, see the FIG. 5.
5) Calculate the coefficient of inhibition on RSV replication and Hh activity (ICrh). The ICrh of S1-4 is 1.6172823, which is larger than 1 and means that it owns beneficial inhibition property, see the FIG. 6.
6) Screening compound S1-4. compound S1-4, with beneficial inhibition property. Furthermore, within the compounds tested, S1-4 owns the largest ICrh data, suggesting that it can be developed to treat RSV infection, see the FIG. 6.

Finally, it should be illustrated that, the examples above is only to explain clearly the case in the invention, and is not to limit the mode of execution. For the normal technician in the field, it can be changed and modified based on the illustration above. Here, it is not necessary and no way to state all the examples with different mode of execution. However, all the obvious change and modification derived from the invention should be protected by the invention.

The invention claimed is:

1. A compound for treating a respiratory syncytial virus infection according to the following structure:

2. A method of treating a respiratory tract infection in a patient comprising administering to the patient the compound of claim 1, wherein the compound does not cause side effects on the patient.

3. The method of claim 2, wherein the respiratory tract infection is caused by a virus.

4. The method of claim 2, wherein the respiratory tract infection is a paramyxovirus infection.

5. The method of claim 2, wherein the respiratory tract infection is a respiratory syncytial virus infection.

6. The method of claim 2, wherein the respiratory tract infection is capillary bronchitis caused by a respiratory syncytial virus.

7. The method of claim 2, wherein the respiratory tract infection is pneumonia caused by a respiratory syncytial virus.

8. The method of claim 2, wherein the respiratory tract infection is tympanitis caused by a respiratory syncytial virus.

* * * * *